(12) United States Patent
Chiang

(10) Patent No.: US 11,291,846 B2
(45) Date of Patent: Apr. 5, 2022

(54) LONG-RANGE WIRELESS CHARGING ENHANCEMENT STRUCTURE FOR IMPLANTABLE MEDICAL DEVICES

(71) Applicant: Orion Biotech Inc., Taipei (TW)

(72) Inventor: Ming-Fu Chiang, Taipei (TW)

(73) Assignee: ORION BIOTECH INC., Taipei (TW)

(*) Notice: Subject to any disclaimer, the term of this patent is extended or adjusted under 35 U.S.C. 154(b) by 590 days.

(21) Appl. No.: 16/003,097

(22) Filed: Jun. 7, 2018

(65) Prior Publication Data
US 2019/0247670 A1    Aug. 15, 2019

(30) Foreign Application Priority Data
Feb. 9, 2018    (TW) .................. 107104581

(51) Int. Cl.
| | |
|---|---|
| *A61N 1/372* | (2006.01) |
| *H02J 7/02* | (2016.01) |
| *H02J 50/40* | (2016.01) |
| *H02J 50/20* | (2016.01) |
| *A61N 1/378* | (2006.01) |
| *H02J 7/00* | (2006.01) |
(Continued)

(52) U.S. Cl.
CPC ....... *A61N 1/37229* (2013.01); *A61N 1/3787* (2013.01); *A61N 1/37223* (2013.01); *H02J 7/0029* (2013.01); *H02J 7/025* (2013.01); *H02J 50/20* (2016.02); *H02J 50/40* (2016.02); *H02J 7/345* (2013.01); *H02J 50/15* (2016.02); *H02J 50/30* (2016.02)

(58) Field of Classification Search
CPC ............ A61N 1/37229; A61N 1/37223; A61N 1/3787; H02J 50/20; H02J 50/40; H02J 50/15; H02J 50/30; H02J 7/0029; H02J 7/025; H02J 7/345
See application file for complete search history.

(56) References Cited

U.S. PATENT DOCUMENTS

| | | | | |
|---|---|---|---|---|
| 5,862,803 A | * | 1/1999 | Besson | ............... H03F 3/45103 |
| | | | | 600/508 |
| 2008/0154178 A1 | * | 6/2008 | Carter | .................... H02J 50/10 |
| | | | | 604/20 |
(Continued)

FOREIGN PATENT DOCUMENTS

| | | |
|---|---|---|
| JP | 2014-501139 A | 1/2014 |
| JP | 2014-522218 A | 8/2014 |
(Continued)

*Primary Examiner* — Catherine M Voorhees
*Assistant Examiner* — Roland Dinga
(74) *Attorney, Agent, or Firm* — Cheng-Ju Chiang (57) ABSTRACT

A long-range wireless charging enhancement structure for implantable medical devices (IMDs) is disclosed. The abovementioned enhancement structure provides a possibility for long-range charging the IMDs, which maintains the quality of user's lives and also reduces the risks of replacing the batteries through surgeries. The enhancement structure includes an enhancer, which comprises an emitter, a carrier, an IMD, and an enhancement module. The enhancement module is set within the carrier and disposed at the outer surface of user's skin between the emitter and the IMD. The charging signals emitted by the emitter is enhanced by the enhancement module and further transmitted for charging the IMD inside the user's tissue.

11 Claims, 6 Drawing Sheets

(51) Int. Cl.
  *H02J 50/30*   (2016.01)
  *H02J 7/34*    (2006.01)
  *H02J 50/15*   (2016.01)

(56) References Cited

U.S. PATENT DOCUMENTS

| | | | |
|---|---|---|---|
| 2010/0160712 A1* | 6/2010 | Burnett | A61N 1/36017 600/13 |
| 2010/0305663 A1* | 12/2010 | Aghassian | A61N 1/37247 607/61 |
| 2015/0048790 A1 | 2/2015 | Rudser et al. | |
| 2016/0241087 A1* | 8/2016 | Bae | H02J 50/60 |
| 2017/0201099 A1* | 7/2017 | Savanth | G05B 15/02 |
| 2019/0201700 A1* | 7/2019 | Lui | H02J 50/10 |

FOREIGN PATENT DOCUMENTS

| | | |
|---|---|---|
| JP | 2015-122811 A | 7/2015 |
| JP | 2016-535578 A | 11/2016 |
| JP | 2017-164576 A | 9/2017 |
| JP | 2017-205428 A | 11/2017 |
| JP | 2019-500065 A | 1/2019 |
| JP | 2019-510463 A | 4/2019 |
| WO | 2016/123069 A1 | 8/2016 |

\* cited by examiner

LONG-RANGE WIRELESS CHARGING ENHANCEMENT STRUCTURE FOR IMPLANTABLE MEDICAL DEVICES

CROSS-REFERENCE TO RELATED APPLICATION AND CLAIM OF PRIORITY

This application claims the benefit of Taiwan Patent Application No. 107104581, filed on Feb. 9, 2018, in the Taiwan Intellectual Property Office, the disclosure of which is incorporated herein in its entirety by reference.

TECHNICAL FIELD

At least one embodiment of the present invention relates to wireless charging enhancement structure for implantable medical devices. More particularly, at least one embodiment of the present invention relates to long-range wireless charging enhancement structure for implantable medical devices.

DESCRIPTION OF THE RELATED ART

The technique related to disease treatments with implantable medical devices (IMDs) has been well developed for years, such as Parkinson's disease (PD) treatment with deep brain stimulation (DBS) and heart disease treatment with artificial pacemaker. Particularly, active implantable medical devices (AIMD) are powered by batteries for the functionality. However, the electric energy stored in these batteries is only available for operating these implantable medical devices from 5 to 10 years. Once the batteries are completely consumed, it is necessary to replace them via surgeries. However, the abovementioned ways are not only inconvenience for users, but also financial burden due to surgery costs. Moreover, the risks of surgeries are considerable, since among the users suffering from these diseases, and the proportion of the elderly is quite high.

The present technology has been able to charge these active implantable medical devices (AIMD) wirelessly. The most common technique is to charge through inductive coupling of inductive coils by placing a receiving coil in the implantable medical device and a charging coil in a position close to the receiving coil outside the skin. Nevertheless, the inductive coils cannot be separated for more than a few centimeters, and the user would have to carry the charging coil with belts to keep it close enough to the implantable medical device and it may discomfort the user no matter on usual life or the mental aspect.

The other common technique is to charge through resonant inductive coupling which can wirelessly charge the implantable medical devices in a distance of 1 to 2 meters. However the sizes of the coils are relatively larger in order for oscillation frequencies of the charging coil and the inductive coil to match. It is not ideal for the use of implantable medical devices. Also, the output power is larger and may cause safety issues for medical use. Furthermore, it may not comply with regulations.

SUMMARY

To solve the aforesaid problems of the prior art, at least one embodiment of the present invention provides a long-range wireless charging enhancement structure for implantable medical devices comprising an emitter, a carrier, an implantable medical device and an enhancement module.

The emitter is configured to emit a plurality of charging signals. The carrier is arranged outside of a user's skin on one side of the emitter and the implantable medical device is arranged on the other side of the carrier relative to the emitter. And the enhancement module is arranged in the carrier.

Moreover, the plurality of charging signals are received by the enhancement module and transformed into a plurality of enhanced signals, and the implantable medical device receive the plurality of enhanced signals.

The preceding brief account of the present invention is intended as a preliminary description of the various aspects and technical features of the invention, showing the various concepts of the invention only concisely. The brief account is neither a detailed description nor intended to include all the key or essential elements of the invention or define the scope of the invention.

DESCRIPTION OF THE PREFERRED EMBODIMENTS

The examples depicted in the following section are provided for the purpose of detailed explanation of the features of preferred embodiments, in order to enable the person having ordinary skill in the art to understand the preferred embodiments. It is to be understood that the specifications provided in the drawings are merely for the purposes of illustration and that various changes without departing from the spirit and intention may be included or implied in the present invention.

Figure 1:
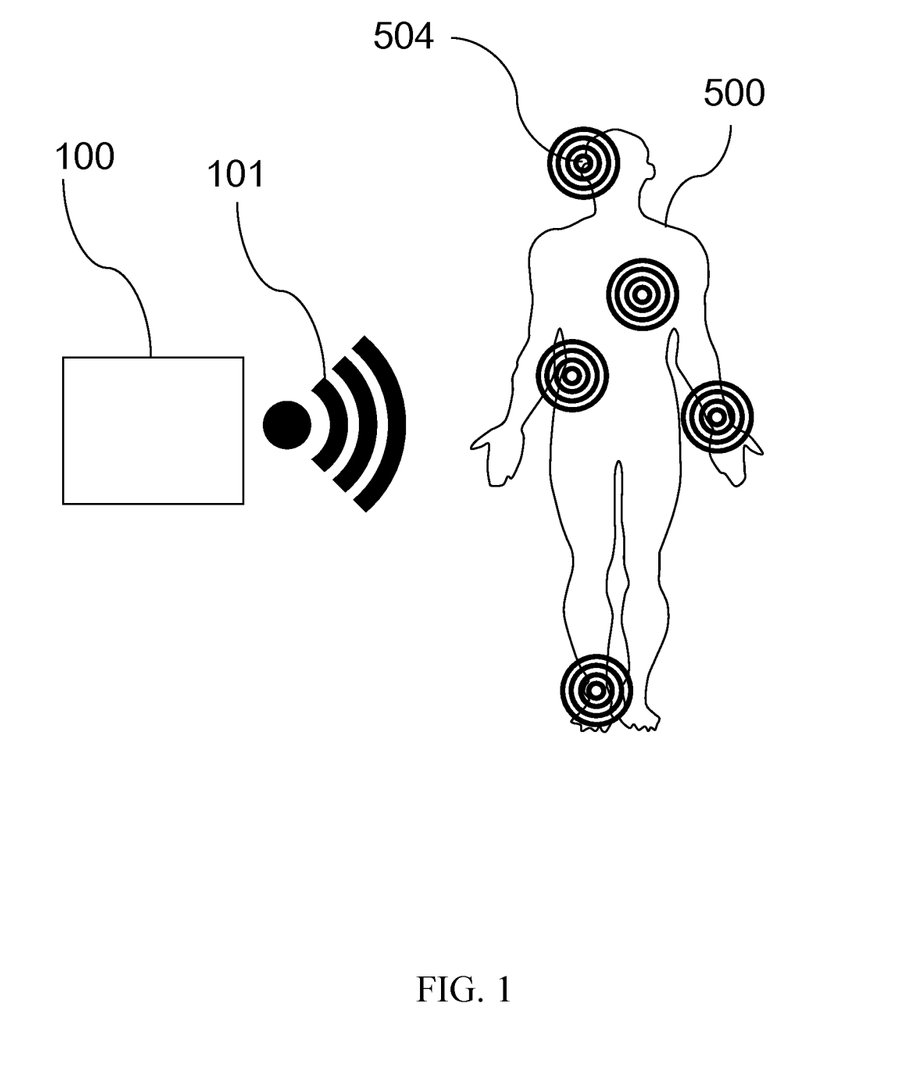
FIG. 1 is a schematic diagram illustrating a wireless charging technique for implantable medical devices for implantable medical devices, in accordance with some embodiments of the present invention.

FIG. 1 is a schematic diagram illustrating a wireless charging technique for implantable medical devices, in accordance with some embodiments of the present invention. As illustrated in FIG. 1, an emitter 100 emits and sends out a plurality of charging signals 101. The plurality of charging signals 101 propagates in space and reaches a position of a user 500 and charges the medical device implanted in the target 504, which is the body tissue or the affected area of the disease equipped with the implantable medical device. In this embodiment, the plurality of charging signals 101 sent from the emitter 100 simultaneously charge all the medical devices in more than one target 504. Therefore, when the user 500 is implanted with multiple active implantable medical devices in more than one affected area, these active implantable medical devices can be simultaneously charged through the technique in the present invention.

In an embodiment of the present invention, the emitter 100 is a radio frequency transmitter, and the plurality of charging signals 101 emitted by the emitter 100 are electromagnetic signals. In another embodiment of the present invention, the emitter 100 is an infrared laser transmitter, and the plurality of charging signals 101 emitted by the emitter 100 are infrared signals with directivity and wavelength of 700~900 nm. Preferably, the wavelength of the infrared signal is 800 nm. In the other embodiment of the present invention, the emitter 100 is an ultrasonic transmitter. Thus the plurality of charging signals 101 transmitted by the emitter 100 are ultrasonic signals. In a preferred embodiment of the present invention, the implantable medical device is an active implantable medical device, and the range for wireless charging is from 10 cm to several meters. The user 500 can move freely in a larger space without disturbing the activities of their daily living. The active implantable medical device may be an implanted medical device that requires external power input for its operation, such as a cardiac monitor, a cardiac pacemaker or a brain stimulator.

Figure 2:
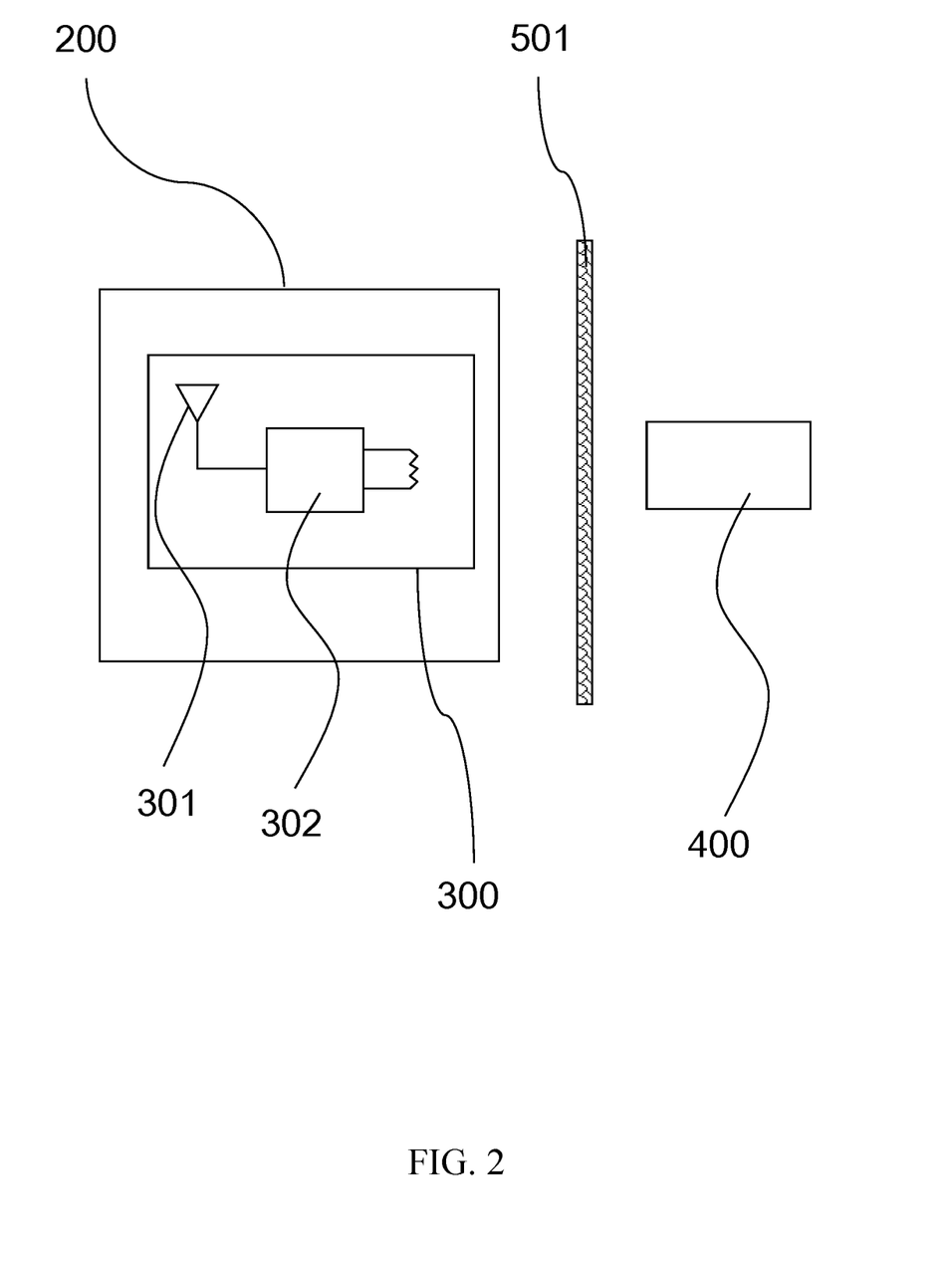
FIG. 2 is a schematic diagram illustrating a long-range wireless charging enhancement structure for implantable medical devices, in accordance with some embodiments of the present invention.

Referring to FIG. 1 and FIG. 2, which is a schematic diagram illustrating a long-range wireless charging enhancement structure for implantable medical devices in accordance with some embodiments of the present invention. As shown in the figures, the long-range wireless charging enhancement structure for implantable medical devices in accordance with the embodiment of the present invention comprises an emitter 100 for emitting a plurality of charging signals 101, a carrier 200 arranged outside skin 501 of a user 500 on one side of the emitter 100, an implantable medical device 400 arranged on the other side of the carrier 200 relative to the emitter 100 and an enhancement module 300 arranged in the carrier 200. Moreover, the plurality of charging signals 101 are received by the enhancement module 300 and transformed into a plurality of enhanced signals, and the implantable medical device 400 receives the plurality of enhanced signals.

Please refer to FIG. 1 and FIG. 2 at the same time. In some embodiments of the present invention, the carrier 200 is an accessory, a patch, a sticky dressing, a magnetic device, or a chip card. The user 500 may wear an accessory provided with the carrier 200 near the target 504, such as a necklace, a belt buckle, a bracelet, an anklets, etc., to enhance the plurality of charging signals 101 and charge the implantable medical device 400 positioned at the target 504. The user 500 can also attaching a patch or a sticky dressing provided with the carrier 200 to the skin 501 near the target 504 to enhance the plurality of charging signals 101 and charge the implantable medical device 400 positioned at the target 504. Other embodiments of the carrier 200 of the present invention may include but not limited to a chip card, a magnetic device, or anything that could be carried near the target 504 easily. In addition, the carrier 200 can be implemented as an array to increase the receiving surface area, and the present invention is not limited thereto.

In another preferred embodiment of the present invention, the carrier 200 is a textile and the enhancement module 300 is mounted, imbedded, weaved or knitted into the carrier 200. Detailed description of the preferred embodiments: weaving or knitting more than one type of weaving threads containing electrically conductive material into a cloth by a special weaving or knitting technique and making a specific area of the cloth possess the function of enhancing the plurality of charging signals 101. The abovementioned specific area of the cloth serves as the enhancement module 300 of the present invention and the cloth made of the electrically conductive threads serves as the carrier 200 of the present invention. The user 500 wears a cloth or a hat weaved or knitted to include the carrier 200 near the target 504 to enhance the plurality of charging signals 101 and to further charge the implantable medical device 400 arrange at the target 504.

In another embodiment, the carrier 200 is a textile, and the enhancement module 300 is a plurality of radio frequency antenna arrays. The plurality of radio frequency antenna arrays are weaved or knitted into the carrier 200 by a special weaving or knitting technique to enhance the electromagnetic waves, which are regarded as the charging signals. The above description of the embodiments is only for the purpose of simply illustrating the concept of the present invention. Those skilled in the art should understand that any simple equivalent changes and modifications are still within the scope of the present invention, and are not limited to the description.

In the embodiment shown in FIG. 2, an enhancement module 300 is disposed in the carrier 200. The enhancement module 300 may be divided into two parts: a receiver 301 and a processing module 302. In some embodiments, in order for the enhancement module 300 to enhance the plurality of charging signals 101 (for example, the electromagnetic signal, the infrared signal or the ultrasonic signal, etc.) provided by any type of receiver 301, the enhancement module 300 may be implemented as combinations of multiple receivers 301 and processing modules 302. When the plurality of charging signals 101 are electromagnetic signals, the receiver 301 is a plurality of radio frequency antenna arrays. When the plurality of charging signals 101 are infrared signals, the receiver 301 is a photovoltaic element. When the plurality of charging signals 101 are ultrasonic signals, the receiver 301 is a dielectric film. In one embodiment of the present invention, the dielectric film comprises a plurality of dielectric layers, wherein the dielectric constants of each dielectric layer are different.

In an embodiment of the present invention, the receiver 301 is a combination of a plurality of radio frequency antenna arrays, dielectric films and photovoltaic elements, and the processing module 302 is configured with a signal conditioner. When the plurality of charging signals 101 are electromagnetic signals, the signal conditioner identifies the signals and designates the plurality of radio frequency antenna arrays in the receiver 301 to enhance the plurality of charging signals 101 and trigger the corresponding circuits in the processing module 302 to process the plurality of enhanced signals. When the plurality of charging signals 101 are infrared signals, the signal conditioner identifies the signals, and designates the plurality of photovoltaic elements in the receiver 301 to enhance the plurality of charging signals 101 and trigger the corresponding circuits in the processing module 302 to process the enhanced signals. When the plurality of charging signals 101 are ultrasonic signals, the signal conditioner identifies the signals and designates the plurality of dielectric films in the receiver 301 to enhance the plurality of charging signals 101 and trigger the corresponding circuits in the processing module 302 to process the enhanced signals.

Figure 4:
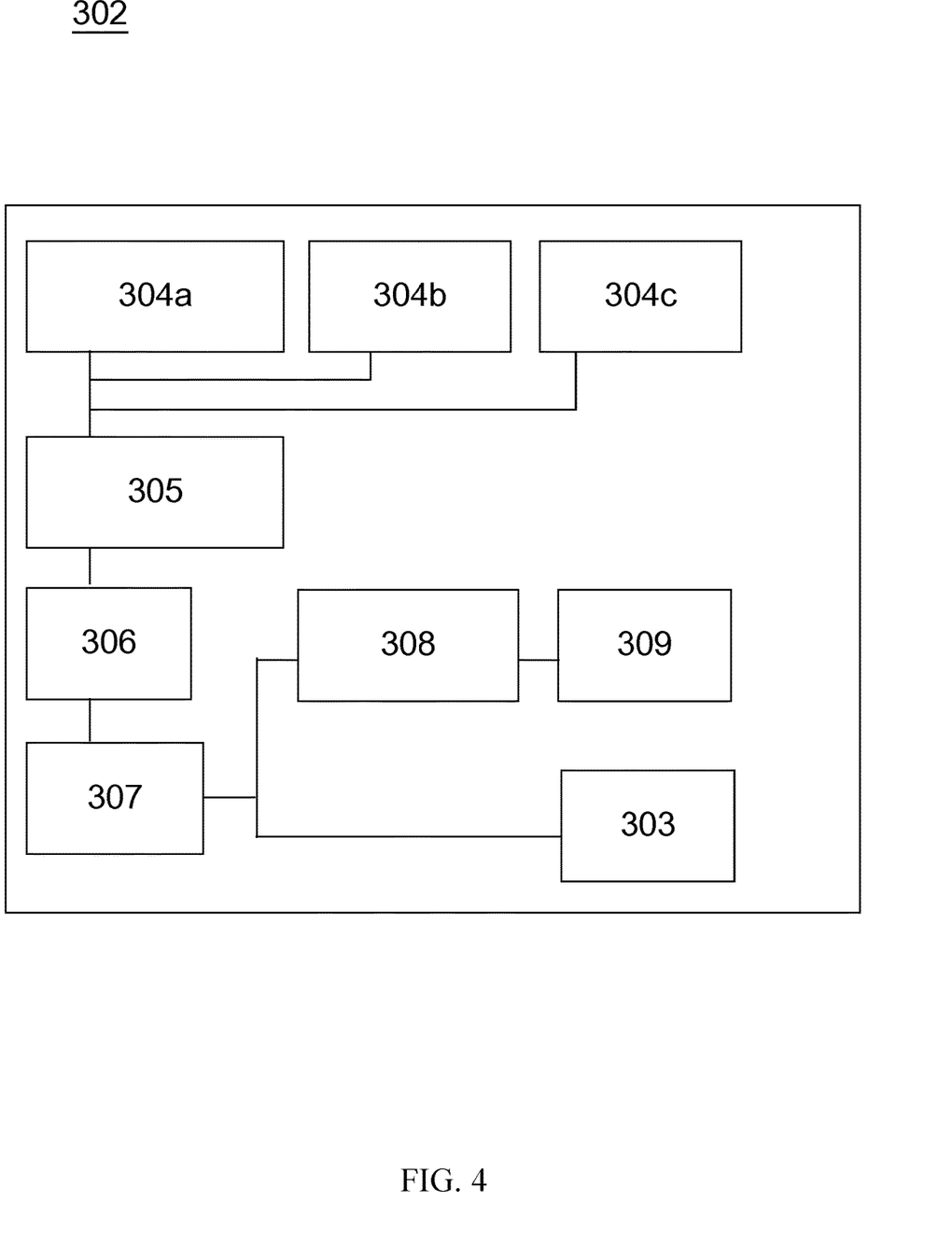
FIG. 4 is a block diagram illustrating an enhancement module, in accordance with some embodiments of the present invention.

Please refer to FIG. 2 and FIG. 4. In an embodiment of the present invention, the receiver 301 is a plurality of radio frequency antenna arrays, a dielectric film, a photovoltaic element, or any combination thereof. The processing module 302 comprises a radio frequency receiver 304a connected with the receiver 301, an impedance matching loop 305 connected with the radio frequency receiver 304a, a rectifier 306 connected with the impedance matching loop 305, a voltage boosting circuit 307 connected with the rectifier 306, a battery protection circuit 308 connected with the voltage boosting circuit 307, an energy storage device 309 connected with the battery protection circuit 308 and an output module 303 connected with the energy storage device 309.

Please refer to FIG. 2 and FIG. 4. In an embodiment of the present invention, the receiver 301 is a plurality of radio frequency antenna arrays, a dielectric film, a photovoltaic element, or any combination thereof. The processing module 302 comprises a piezoelectric receiver 304b connected with the receiver 301, an impedance matching loop 305 connected with the piezoelectric receiver 304b, a rectifier 306 connected with the impedance matching loop 305, a voltage boosting circuit 307, connected with the rectifier 306, a battery protection circuit 308 connected with the voltage boosting circuit 307, an energy storage device 309 connected with the battery protection circuit 308 and an output module 303 connected with the energy storage device 309.

Please refer to FIG. 2 and FIG. 4. In an embodiment of the present invention, the receiver 301 is a plurality of radio frequency antenna arrays, a dielectric film, a photovoltaic element, or any combination thereof. The processing module 302 comprises a photovoltaic receiver 304c connected with the receiver 301, an impedance matching loop 305 connected with the photovoltaic receiver 304c, a rectifier 306 connected with the impedance matching loop 305, a voltage boosting circuit 307 connected with the rectifier 306, a battery protection circuit 308 connected with the voltage boosting circuit 307, an energy storage device 309 connected with the battery protection circuit 308 and an output module 303 connected with the energy storage device 309.

Please refer to FIG. 2 and FIG. 4. In an embodiment of the present invention, the receiver 301 is a plurality of radio frequency antenna arrays. The processing module 302 comprises a radio frequency receiver 304a connected with the plurality of radio frequency antenna arrays, an impedance matching loop 305 connected with the radio frequency receiver 304a, a rectifier 306 connected with the impedance matching loop 305, a voltage boosting circuit 307 connected with the rectifier 306, a battery protection circuit 308 connected with the voltage boosting circuit 307, an energy storage device 309 connected with the battery protection circuit 308 and an output module 303 connected with the energy storage device 309.

Please refer to FIG. 2 and FIG. 4. In another embodiment of the present invention, the receiver 301 is a dielectric film. The processing module 302 comprises a piezoelectric receiver 304b connected with the dielectric film, an impedance matching loop 305 connected with the piezoelectric receiver 304b, a rectifier 306 connected with the impedance matching loop 305, a voltage boosting circuit 307 connected with the rectifier 306, a battery protection circuit 308 connected with the voltage boosting circuit 307, an energy storage device 309 connected with the battery protection circuit 308 and an output module 303 connected with the energy storage device 309. In a preferred embodiment of the present invention, the dielectric film is a piezoelectric dielectric film. In a more preferred embodiment, the dielectric film may be a combination of progressive piezoelectric dielectric layers, which is not limited in the present invention. The aforementioned progressive piezoelectric dielectric layers have different impedances and penetration coefficients, and the transmittances of the plurality of charging signals 101 is adjusted to a desired range by connecting the progressive piezoelectric dielectric layers in series or in parallel. In an embodiment, the ultrasonic charging signals 101 can be adjusted to an intensity of 600-900 milliwatts per square centimeter after passing through the dielectric film. In a preferred embodiment, the ultrasonic charging signals 101 can be further adjusted to a strength of 700 milliwatts per square centimeter (700 mW/cm$^2$), which not only provides a sufficiently high charging energy, but also provides an energy intensity that conforms to the safety regulations applied to human body.

Please refer to FIG. 2 and FIG. 4. In an embodiment of the present invention, the receiver 301 is a photovoltaic element. The processing module 302 comprises a photovoltaic receiver 304c connected with the photovoltaic element, an impedance matching loop 305 connected with the photovoltaic receiver 304c, a rectifier 306 connected with the impedance matching loop 305, a voltage boosting circuit 307 connected with the rectifier 306, a battery protection circuit 308 connected with the voltage boosting circuit 307, an energy storage device 309 connected with the battery protection circuit 308 and an output module 303 connected with the energy storage device 309.

Figure 3:
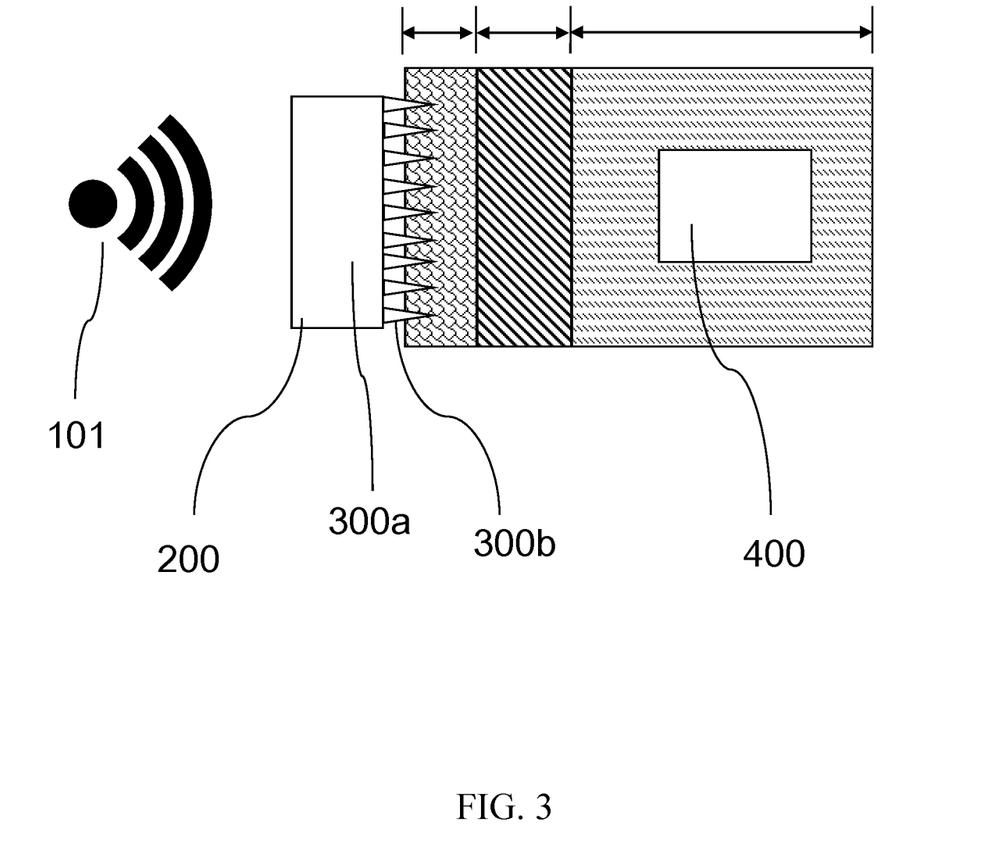
FIG. 3 is a schematic diagram illustrating a long-range wireless charging enhancement structure for implantable medical devices, in accordance with some embodiments of the present invention.

Please refer to FIG. 3. FIG. 3 is a schematic diagram illustrating a long-range wireless charging enhancement structure for implantable medical devices in accordance with some embodiments of the present invention. The long-range wireless charging enhancement structure for implantable medical devices in accordance with the embodiment of the present invention comprises an emitter 100 for emitting a plurality of charging signals 101, a carrier 200 arranged outside skin 501 of a user 500 on one side of the emitter 100, an implantable medical device 400 arranged on the other side of the carrier 200 relative to the emitter 100 and an enhancement module 300 arranged in the carrier 200. Moreover, the plurality of charging signals 101 are received by the enhancement module 300 and transformed into a plurality of enhanced signals, and the implantable medical device 400 receives the plurality of enhanced signals. The carrier 200 is disposed outside of the skin 501 of a user 500 and the implantable medical device 400 is disposed in a target tissue 502b underneath the skin 501 of the user 500. The target tissue 502b varies with situation which depends on the type of treatment, and the target tissue 502b could be a muscle layer, a skeleton, a visceral organ, or a body cavity.

As shown in FIG. 3, the plurality of charging signals 101 is transmitted through the carrier 200 disposed on the outer surface of the skin 501 and then enhanced by the enhancement module 300 to charge the implantable medical device 400 located in the target tissue 502b. In this embodiment, the enhancement module 300 includes two parts, an attaching part 300a and a microneedle module 300b. The attaching part 300a may be a patch or a sticker made of a conductive film such as copper foil, gold foil or other composite materials that can be attached to the surface of the human body. The microneedle module 300b is a solid or hollow conical structure and is connected to the attaching part 300a. In this way, the microneedle module 300b penetrates into the skin 501 of the user 500. Preferably, the microneedle module 300b in the enhancement module 300 comprise conical, triangular pyramidal or polygonal-based pyramidal microneedle array made from polymer materials. In other possible embodiments, each of the conical or pyramidal microneedles of the microneedle module 300b may also be a cone-shaped or a disc-shaped structure embedded with a metal belt, a metal ring or a metal wire, which is not limited in the present invention.

In an embodiment, the microneedle module 300b in the enhancement module 300 enhances the plurality of charging signals 101 by its specialized structure. In addition, in the preferred embodiment, the microneedle module 300b penetrates into the skin 501 to about the depth of 100 micrometers (μm) to achieve the best effect of transmitting the enhanced signals into the body of user 500. In a preferred embodiment of the present invention, the microneedle module 300b in the enhancement module 300 is made up of microneedle antennae and has the functions of enhancing energy, focusing energy and guiding energy into the body at the same time. In another preferred embodiment, the microneedle module 300b in the enhancement module 300 is formed by conical antennae embedded with a metal belt, a metal ring or a metal wire. The implementation of the specialization of the enhancement module 300 is illustrated in this figure. However, those ordinary skilled in the art should understand that any simple equivalent changes and modifications are still within the scope of the present invention and are not limited to the description.

Please refer to FIG. 4. which is a block diagram illustrating an enhancement module in accordance with some embodiments of the present invention. As shown in the figure, the enhancement module 300 of the present invention comprises a radio frequency receiver 304a, a piezoelectric receiver 304b, a photovoltaic receiver 304c, an impedance matching loop 305 connected with the radio frequency receiver 304a, the piezoelectric receiver 304b and the photovoltaic receiver 304c. The enhancement module 300 of the present invention further comprises a rectifier 306 connected with the impedance matching loop 305, a voltage boosting circuit 307 connected with the rectifier 306, a battery protection circuit 308 connected with the voltage boosting circuit 307, an energy storage device 309 connected with the battery protection circuit 308 and an output module 303 connected with the energy storage device 309. In another preferred embodiment of the present invention, the receiver 301 is an arbitrary combination of a plurality of radio frequency antenna arrays, a dielectric film, and a photovoltaic element. The receiver 301 is connected to the radio frequency receiver 304a, the piezoelectric receiver 304b and the photovoltaic receiver 304c shown in FIG. 4 to receive multi-source charging signals and to charge the implantable medical device 400.

The energy storage device 309 in the present invention is a rechargeable battery, a supercapacitor or the combination thereof. Preferably, the energy storage device 309 is a lithium iron phosphate battery, which is a safe battery without doubts about overheating or explosion. It also has high output power and the capability of up to more than 1000 times of charging/discharging cycles. In this embodiment, the voltage boosting circuit 307 further comprises a switch circuit, which may be a circuit including a transistor. More specifically, the transistor may be a metal-oxide-semiconductor field-effect transistor (MOSFET). The voltage boosting circuit 307 is connected to the energy storage device 309. The enhancement module 300 can selectively charge the rechargeable battery and the supercapacitor in the energy storage device 309 or directly output the enhanced signals for the implantable medical device 400 to use in the user 500 through the setup of switch circuit in the voltage boosting 307.

Figure 5:
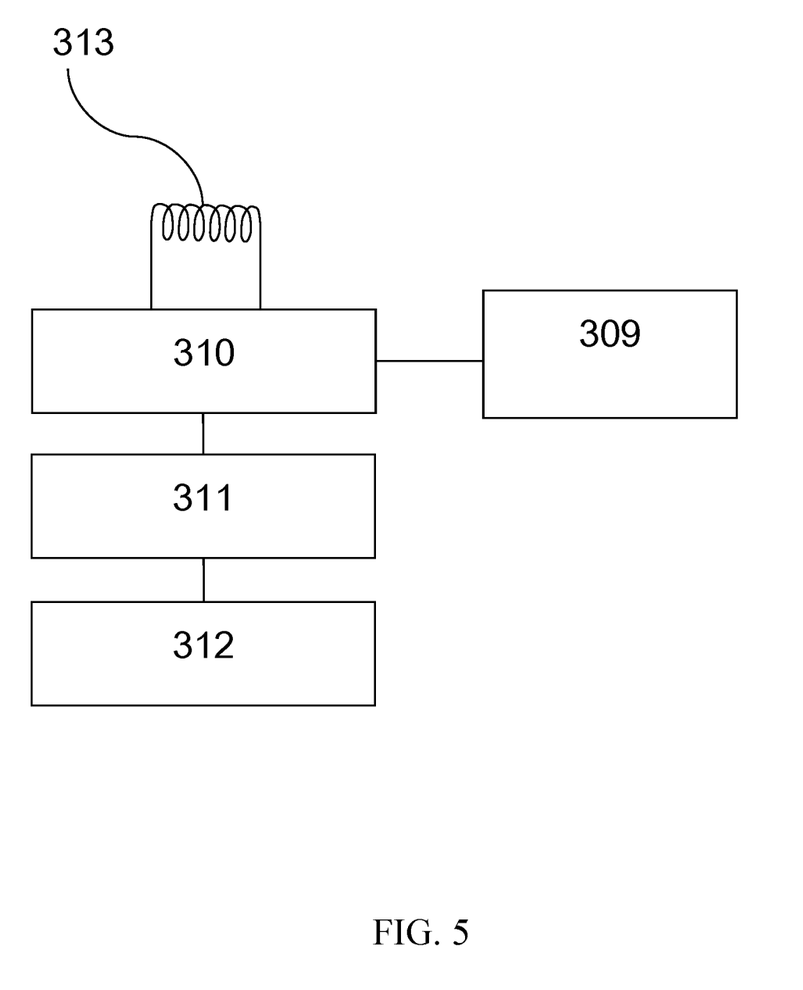
FIG. 5 is a block diagram illustrating an output module, in accordance with some embodiments of the present invention.

Please refer to FIG. 5, which is a block diagram illustrating an output module in accordance with some embodiments of the present invention. As shown in FIG. 5, the output module 303 comprises a DC/AC converting circuit 310 connected with the energy storage device 309, a induction coil 313 connected with the DC/AC converting circuit 310, and an AC signal controlling circuit 311 connected with the DC/AC converting circuit 310, and an AC signal generator 312. In another embodiment of the present invention, the induction coil 313 may be a metal wire or a metal ring mounted or wound on the microneedle module 300b or other special structure of the enhancement module 300. In another embodiment, the induction coil 313 is a conical, triangular pyramidal or polygonal-based pyramidal microneedle antenna structure on the enhancement module 300. The microneedle antenna structure penetrates into the skin 501 and meanwhile the receiving end of the implantable medical device 400 is also set with a correspondingly matched conical, triangular pyramidal or polygonal-based pyramidal antenna structure, and the output module 303 of the enhancement module 300 and the receiving end of the implantable medical device 400 serve as a matched transmit/receive antenna pair to optimize the transfer of energy intensity and conversion efficiency. In addition, the implementation of the induction coil 313 is not limited to that illustrated in the drawings or the description.

Figure 6:
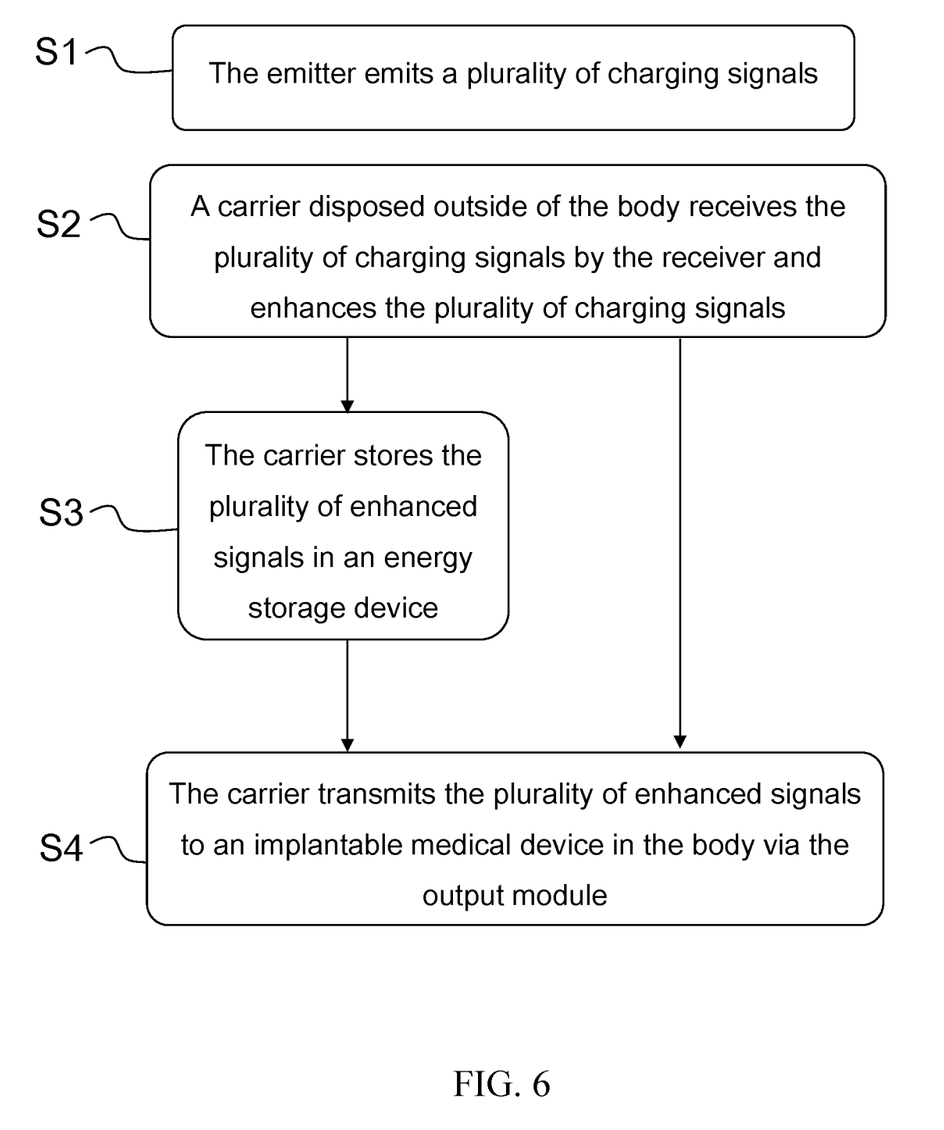
FIG. 6 is a flow chart illustrating a process of long-range wireless charging enhancement technique for implantable medical devices, in accordance with some embodiments of the present invention.

Please refer to FIG. 6, which is flow chart illustrating a process of long-range wireless charging enhancement technique for implantable medical devices in accordance with some embodiments of the present invention. The long-distance wireless charging technology of the implantable medical device in this embodiment includes the following steps. In the step S1, the emitter 100 emits a plurality of charging signals 101. In the step S2, a carrier 200 disposed outside of the body receives the plurality of charging signals 101 by the receiver 301 and enhances the plurality of charging signals. In the step S3, the carrier 200 stores the plurality of enhanced signals in an energy storage device 309. In the step S4, the carrier 200 transmits the plurality of enhanced signals to an implantable medical device 400 in the body via the output module 303. On the other hand, the carrier 200 may also choose not to store the enhanced signal in the energy storage device 309 and transmit the enhanced signal directly to the implantable medical device 400 disposed in the body through the output module 303.

The long-range wireless charging enhancement technique for implantable medical devices of the present invention creates a possibility of lifelong use of the implantable medical devices by introducing the wireless charging enhancement structure so that the user does not have to undergo the expensive and high risk surgery to replace the battery. When the implantable medical device needs to be charged, the user does not have to carry a redundant charging element with him/her. Besides, the user can move freely in a larger area to maintain normal life activities and work while charging and this benefits the user a lot no matter on maintaining the quality of life or on improving the mental health.

There are many inventions described and illustrated above. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

What is claimed is:

1. A long-range wireless charging enhancement structure for implantable medical devices, comprising:

an emitter emitting a plurality of charging signals;

a carrier, deposed outside of a user's skin and on a side of the emitter;

an implantable medical device, arranged on the other side of the carrier relative to the emitter; and an enhancement module, arranged in the carrier;

wherein the enhancement module further comprises at least one receiver;

wherein the at least one receiver comprises a dielectric film;

wherein the dielectric film comprises a plurality of dielectric layers with different dielectric constants;

wherein the plurality of charging signals are received by the enhancement module and transformed into a plurality of enhanced signals, and the implantable medical device receives the plurality of enhanced signals;

wherein the enhancement module comprises a microneedle module;

wherein the microneedle module further comprises conical, triangular pyramidal or polygonal-based pyramidal microneedle array;

wherein microneedles of the microneedle module are cone-shaped or disc-shaped;

wherein the microneedles are embedded with a metal belt, a metal ring or a metal wire.

2. The long-range wireless charging enhancement structure for implantable medical devices according to claim 1, wherein the emitter is a radio frequency transmitter, an infrared laser transmitter or an ultrasonic transmitter.

3. The long-range wireless charging enhancement structure for implantable medical devices according to claim 1, wherein the implantable medical device is an active implantable medical device.

4. The long-range wireless charging enhancement structure for implantable medical devices according to claim 1, wherein the carrier is an accessory, a patch, a sticky dressing, a magnetic device, or a chip card.

5. The long-range wireless charging enhancement structure for implantable medical devices according to claim 4, wherein the carrier is a textile and the enhancement module is imbedded, weaved or knitted into the carrier.

6. The long-range wireless charging enhancement structure for implantable medical devices according to claim 5, wherein the at least one receiver further comprises a plurality of radio frequency antenna arrays, a photovoltaic element or a combination thereof.

7. The long-range wireless charging enhancement structure for implantable medical devices according to claim 6, wherein the enhancement module further comprises:

a radio frequency receiver, connected with the plurality of radio frequency antenna arrays;

an impedance matching loop, connected with the radio frequency receiver;

a rectifier, connected with the impedance matching loop;

a voltage boosting circuit, connected with the rectifier;

a battery protection circuit, connected with the voltage boosting circuit;

an energy storage device, connected with the battery protection circuit; and an output module, connected with the energy storage device.

8. The long-range wireless charging enhancement structure for implantable medical devices according to claim 7, wherein the energy storage device is a rechargeable battery, a supercapacitor or a combination thereof.

9. The long-range wireless charging enhancement structure for implantable medical devices according to claim 8, wherein the output module comprises:

a DC/AC converting circuit, connected with the energy storage device;

an induction coil, connected with the DC/AC converting circuit; and an AC signal controlling circuit, connected with the DC/AC converting circuit; and an AC signal generator.

10. The long-range wireless charging enhancement structure for implantable medical devices according to claim 6, wherein the enhancement module further comprises:

a photovoltaic receiver, connected with the photovoltaic element;

an impedance matching loop, connected with the photovoltaic receiver;

a rectifier, connected with the impedance matching loop;

a voltage boosting circuit, connected with the rectifier;

a battery protection circuit, connected with the voltage boosting circuit;

an energy storage device, connected with the battery protection circuit; and an output module, connected with the energy storage device.

11. The long-range wireless charging enhancement structure for implantable medical devices according to claim 1, wherein the enhancement module further comprises:

a piezoelectric receiver, connected with the dielectric film;

an impedance matching loop, connected with the piezoelectric receiver;

a rectifier, connected with the impedance matching loop;

a voltage boosting circuit, connected with the rectifier;

a battery protection circuit, connected with the voltage boosting circuit;

an energy storage device, connected with the battery protection circuit;

an output module, connected with the energy storage device.

* * * * *